(12) United States Patent
Wang et al.

(10) Patent No.: US 6,384,911 B1
(45) Date of Patent: May 7, 2002

(54) APPARATUS AND METHOD FOR DETECTING ACCURACY OF DRILL HOLES ON A PRINTED CIRCUIT BOARD

(75) Inventors: Guang Shiah Wang, Hsinchu; Chih Yuan Chen, Taipei; Jacky Chen, Yuan Ho; Shi Hsuan Hung, San Chung; Wu Yu Hsiao, Pin Chen, all of (TW)

(73) Assignee: Machvision, Inc., Hsinchu (TW)

(*) Notice: Subject to any disclaimer, the term of this patent is extended or adjusted under 35 U.S.C. 154(b) by 0 days.

(21) Appl. No.: 09/664,777

(22) Filed: Sep. 19, 2000

(51) Int. Cl.$^7$ ............................................. G01N 21/00
(52) U.S. Cl. ................................................ 356/237.6
(58) Field of Search ........................ 356/237.1, 241.1, 356/237.6, 394, 614

(56) References Cited

U.S. PATENT DOCUMENTS

| | | | | |
|---|---|---|---|---|
| 4,145,714 A | * | 3/1979 | MacDonald et al. | 358/106 |
| 4,555,798 A | * | 11/1985 | Broadbent, Jr. et al. | 382/8 |
| 4,560,273 A | * | 12/1985 | Ando et al. | 356/237 |
| 4,596,037 A | * | 6/1986 | Bouchard et al. | 382/8 |
| 5,015,097 A | * | 5/1991 | Nomoto et al. | 356/394 |
| 5,161,202 A | * | 11/1992 | Kitakado et al. | 382/8 |
| 5,185,638 A | * | 2/1993 | Conzola et al. | 356/237 |
| 5,625,193 A | * | 4/1997 | Broude et al. | 250/372 |
| 6,169,603 B1 | * | 1/2001 | Takayama | 356/500 |

* cited by examiner

*Primary Examiner*—Frank G. Font
*Assistant Examiner*—Michael P. Stafira
(74) *Attorney, Agent, or Firm*—Rosenberg, Klein & Lee

(57) ABSTRACT

The present invention proposes an apparatus and a method for detecting the accuracy of drilled holes on a PCB, which can detect the positions, sizes, counts, and wall roughness of drilled holes on a PCB. The apparatus comprises an optical scanning tool and a platform situated below the optical scanning tool. The optical scanning tool can be positioned and moved. Two projecting light sources of parallel light beam are installed thereon to project light to the PCB. A signal receiver is installed between the two projecting light sources. A magnification lens is installed below the signal receiver. The signal receiver receives the light signal of the two projecting light sources reflected from the PCB via the magnification lens. The platform is used to place the PCB. The platform can move with respect to the optical scanning tool to control the distance between the optical scanning tool and the platform. Through the reception of reflected light signals from different positions of the PCB by the signal receiver, the data of drilled holes on the PCB can be calculated out by a computer.

2 Claims, 5 Drawing Sheets

APPARATUS AND METHOD FOR DETECTING ACCURACY OF DRILL HOLES ON A PRINTED CIRCUIT BOARD

FIELD OF THE INVENTION

The present invention relates to an apparatus and a method for detecting the accuracy of drilled holes on a printed circuit board (PCB) and, more particularly, to an apparatus and a method, which can quickly and accurately detect the accuracy of drilled holes on a PCB.

BACKGROUND OF THE INVENTION

In prior art, there are two types of apparatuses for detecting drilled holes on a PCB. For the first type of apparatus, a PCB is placed on an optically-scanned conveying belt. Through the movement of the conveying belt, various data of the drilled holes on the PCB can be scanned out via an optical scanning tool and transferred to a processing unit to check whether they conform to stored data. However, because an accurate positioning procedure is absent from this type of apparatus, only the counts and sizes of drilled holes can be detected. The errors of positions of drilled holes and the burrs and distortions arising from drilling process can not be detected. For the second type of apparatus, detection is performed through the help of position data of drilled holes stored in a computer aided design (CAD) tool or a drilling/processing program. A charge-coupled device (CCD) camera is gradually moved to detect one hole by one hole. Although the positions, sizes, and counts of drilled holes can be detected, the speed is limited by the counts of drilled holes and the distances between them. Moreover, because time is required for moving to and then positioning each drilled hole, the detection speed will be very slow.

Furthermore, due to increased demand in use, the required accuracy of a PCB becomes higher and higher, and the counts of drilled holes thereon become more and more. The above way of using an optically-scanned conveying belt can not satisfy the required accuracy of drilled holes. Once a drilled hole has a slight error, the PCB may be useless. On the other hand, the above way of using position data of drilled holes stored in a CAD tool to position an optical scanning tool is also inapplicable. When there are a lot of drilled holes, it will take much time, resulting in much lower throughput than that of a drilling machine.

The present invention aims to provide an apparatus and a method for detecting the accuracy of drilled holes on a PCB to resolve the above problems.

SUMMARY AND OBJECTS OF THE PRESENT INVENTION

The primary object of the present invention is to provide an apparatus and a method for detecting the accuracy of drilled holes on a PCB so that quick scanning of drilled holes on a PCB can be achieved.

The second object of the present invention is to provide an apparatus and a method for detecting the accuracy of drilled holes on a PCB so that the positions of drilled holes can be accurately detected.

Another object of the present invention is to provide an apparatus and a method for detecting the accuracy of drilled holes on a PCB so that the sizes of drilled holes can be accurately detected.

Yet another object of the present invention is to provide an apparatus and a method for detecting the accuracy of drilled holes on a PCB so that the counts of drilled holes can be accurately detected.

Still yet another object of the present invention is to provide an apparatus and a method for detecting the accuracy of drilled holes on a PCB so that the wall roughness of drilled holes can be accurately detected.

The various objects and advantages of the present invention will be more readily understood from the following detailed description when read in conjunction with the appended drawings, in which:

DETAILED DESCRIPTION OF PREFERRED EMBODIMENT

Figure 1:
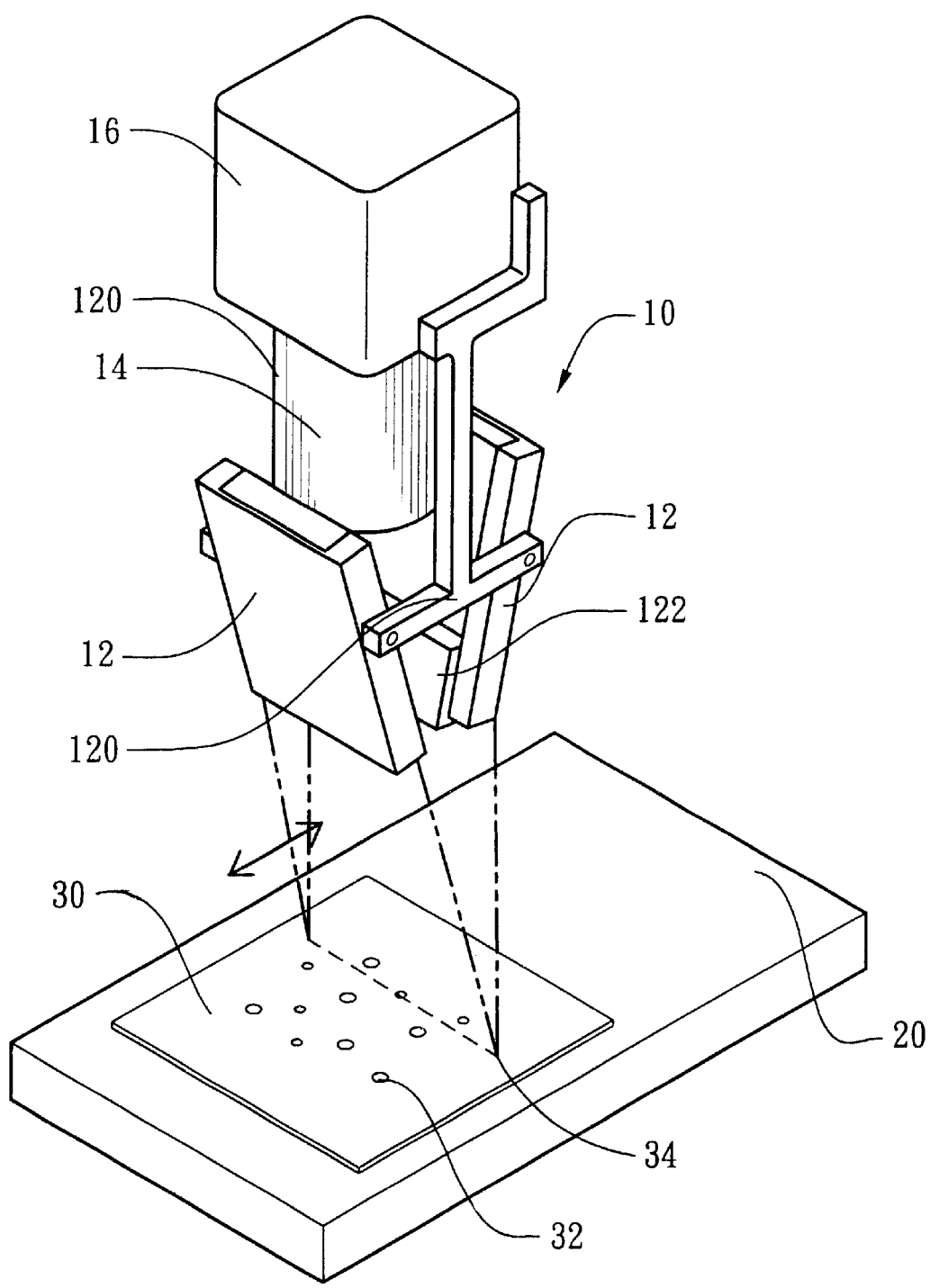
FIG. 1 is a perspective view of the present invention.

As shown in FIG. 1, an apparatus for detecting the accuracy of drilled holes on a PCB comprises an optical scanning tool 10 and a platform 20 situated below the optical scanning tool 10. A signal receiver 16 is installed on the optical scanning tool 10 to receive reflected light signal and is combined with an adjustable and movable structure. A magnification lens 14 is installed below the signal receiver 16. A pair of angle-adjusting supports 120 are installed at two sides of the signal receiver 16 for connecting two projecting light sources 12. Through the upward and downward movement of the angle-adjusting supports 120 and the adjustment of the angles of the two projecting light sources, the signal receiver 16 can receive the best signal via the magnification lens 14. The best received signal is the reflected light of a focused light beam 34 of the projecting light sources 12 from an article to be detected such as a PCB 30. The PCB 30 is placed on the platform 20 and can make orthogonal movements, as shown in the figure, with respect to the optical scanning tool 10 or the focused light beam 34. The way of movement can be that the platform 20 moves while the optical scanning tool 10 is still or that the optical scanning tool 10 moves while the platform 20 is still. Thereby, the optical scanning tool 10 can scan drilled holes 32 on the PCB 30.

Figure 2:
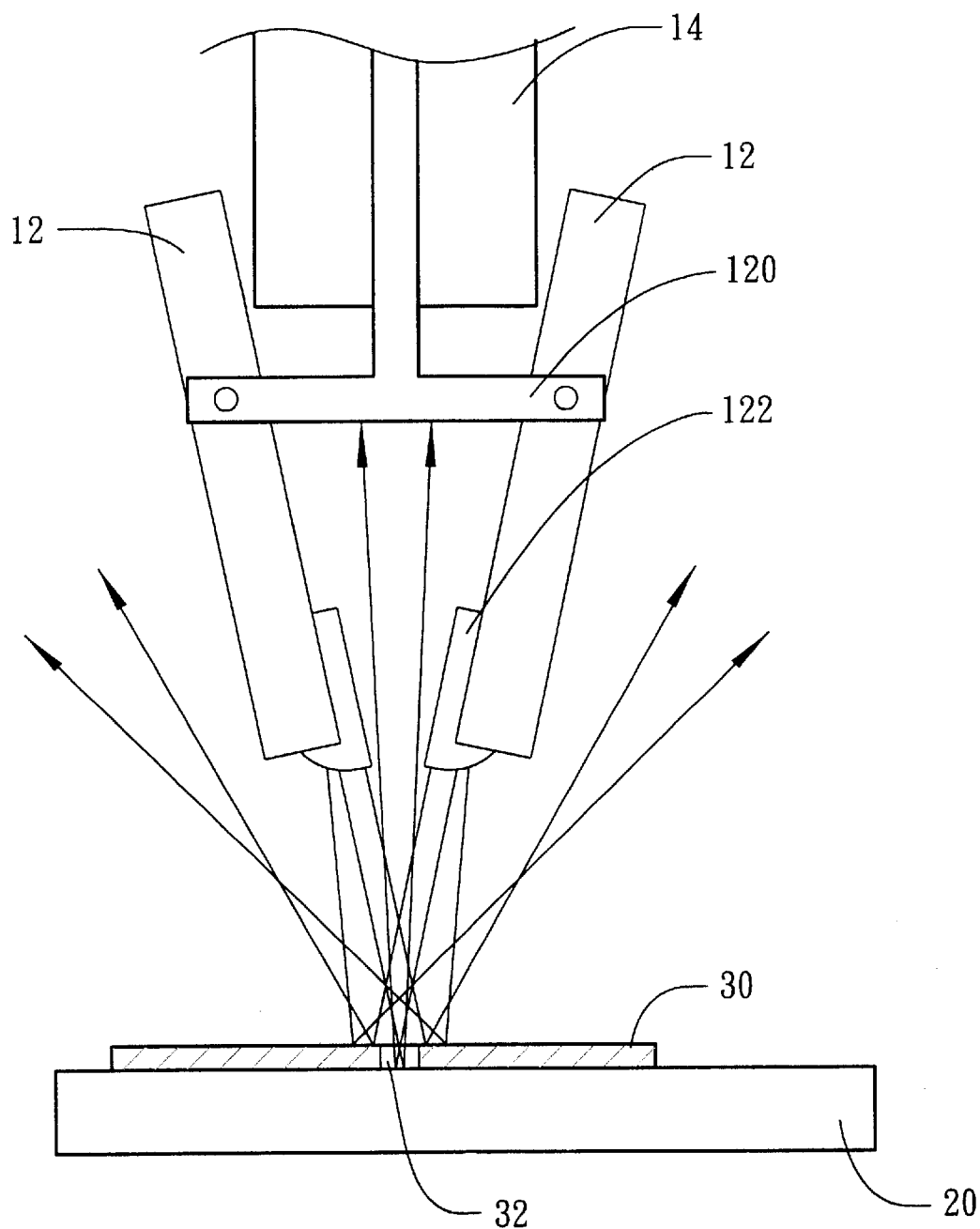
FIG. 2 is a perspective view of an optical scanning tool of the present invention.

As shown in FIG. 2, a lens 122 is installed on each of the two projecting light sources 12 on the optical scanning tool 10. The light beam from the light sources 12 will be projected toward the PCB 30 via the lenses 122. The existence, angle, intensity, and degree of scattering of the reflected light will be measured. The reflected light is received by the signal receiver 16 via the magnification lens 14 to obtain the images of the drilled holes 32. Based on the relative relation between the images and the platform 20, the positions, sizes, counts, and wall roughness of the drilled holes 32 can be calculated out. The results can then be compared with the original design data to judge the quality of the drilled holes 32 on the PCB 30.

Figure 3:
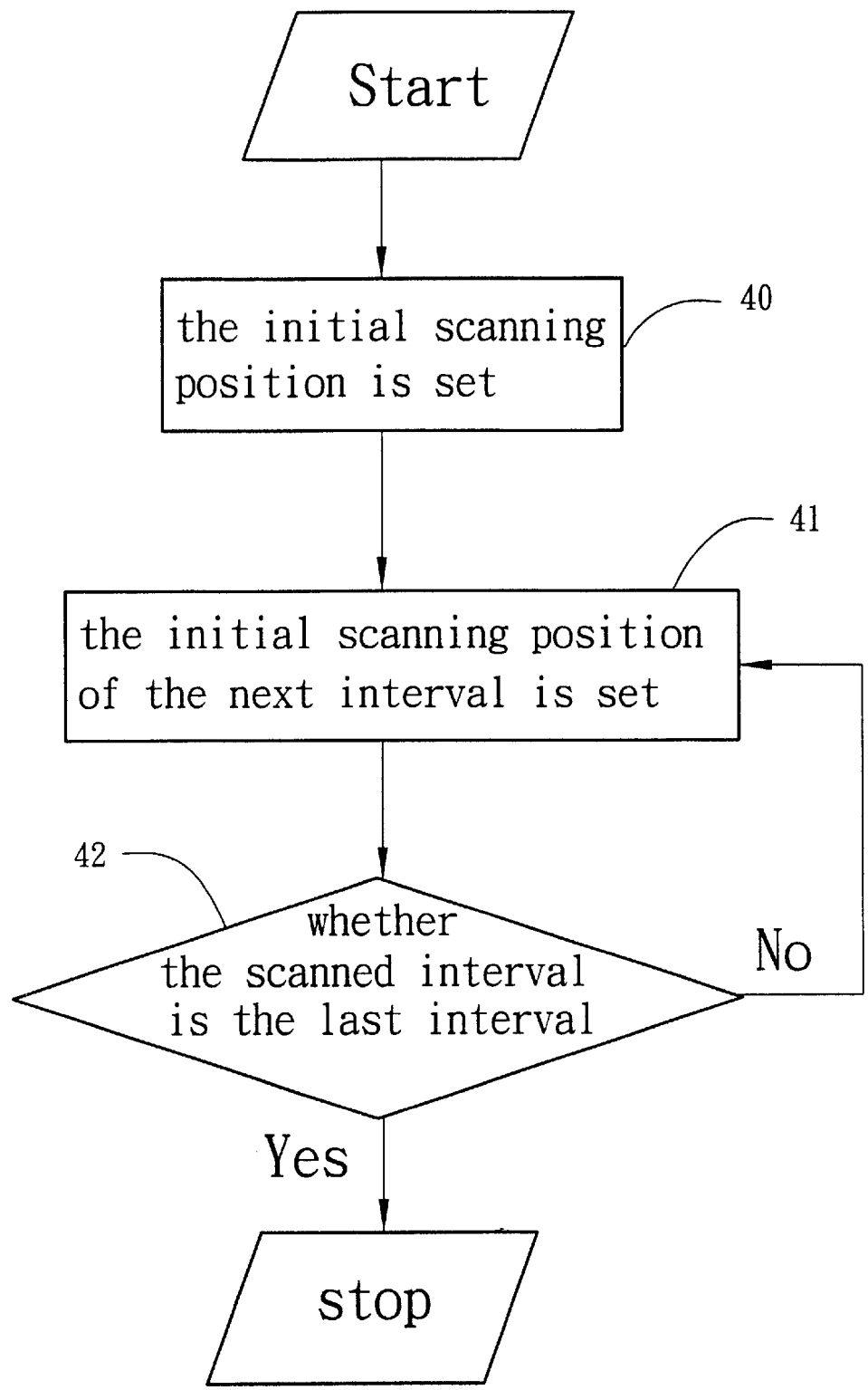
FIG. 3 is a flowchart of the proposed detecting method of the present invention.
Figure 4:
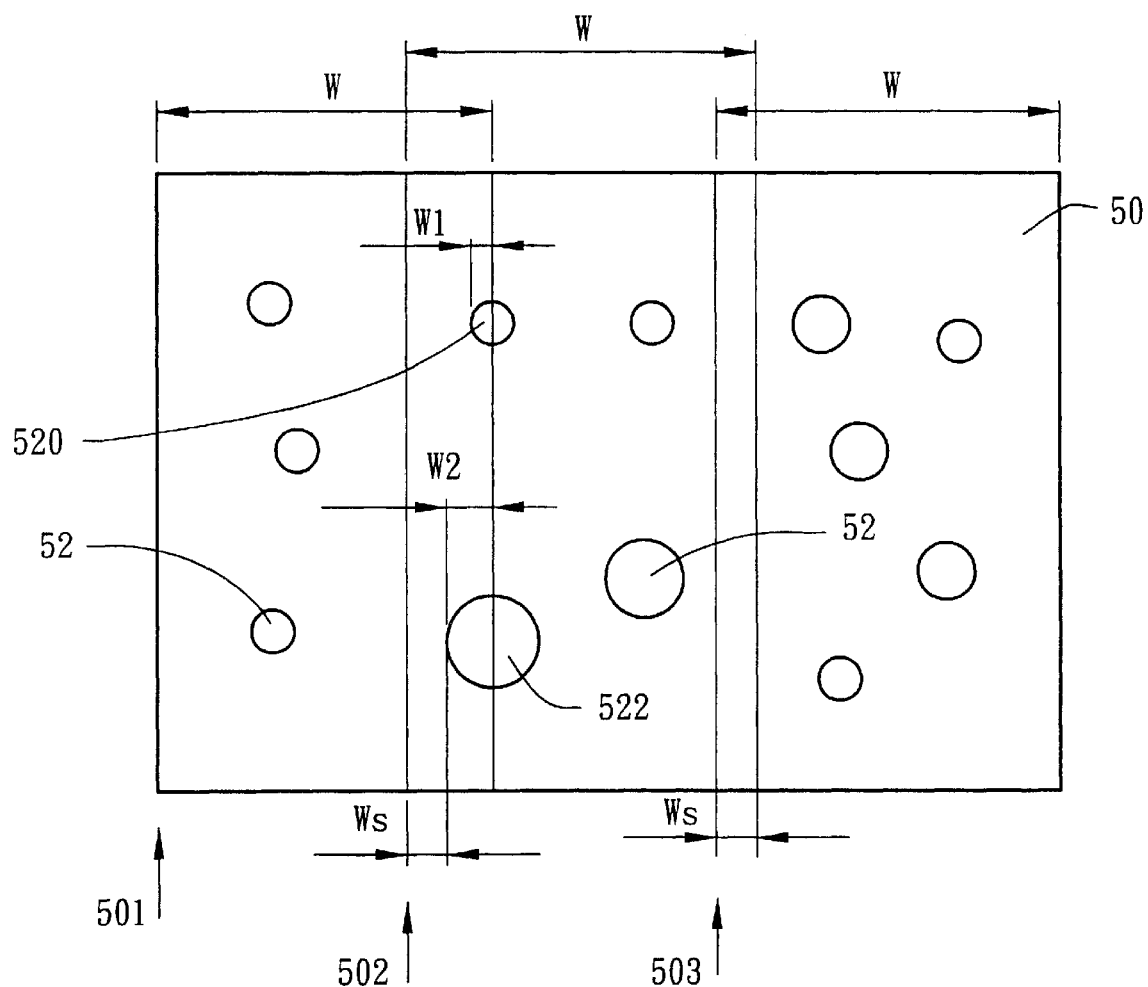
FIG. 4 is a diagram showing how to set intervals according to a preferred embodiment of the present invention.
Figure 5:
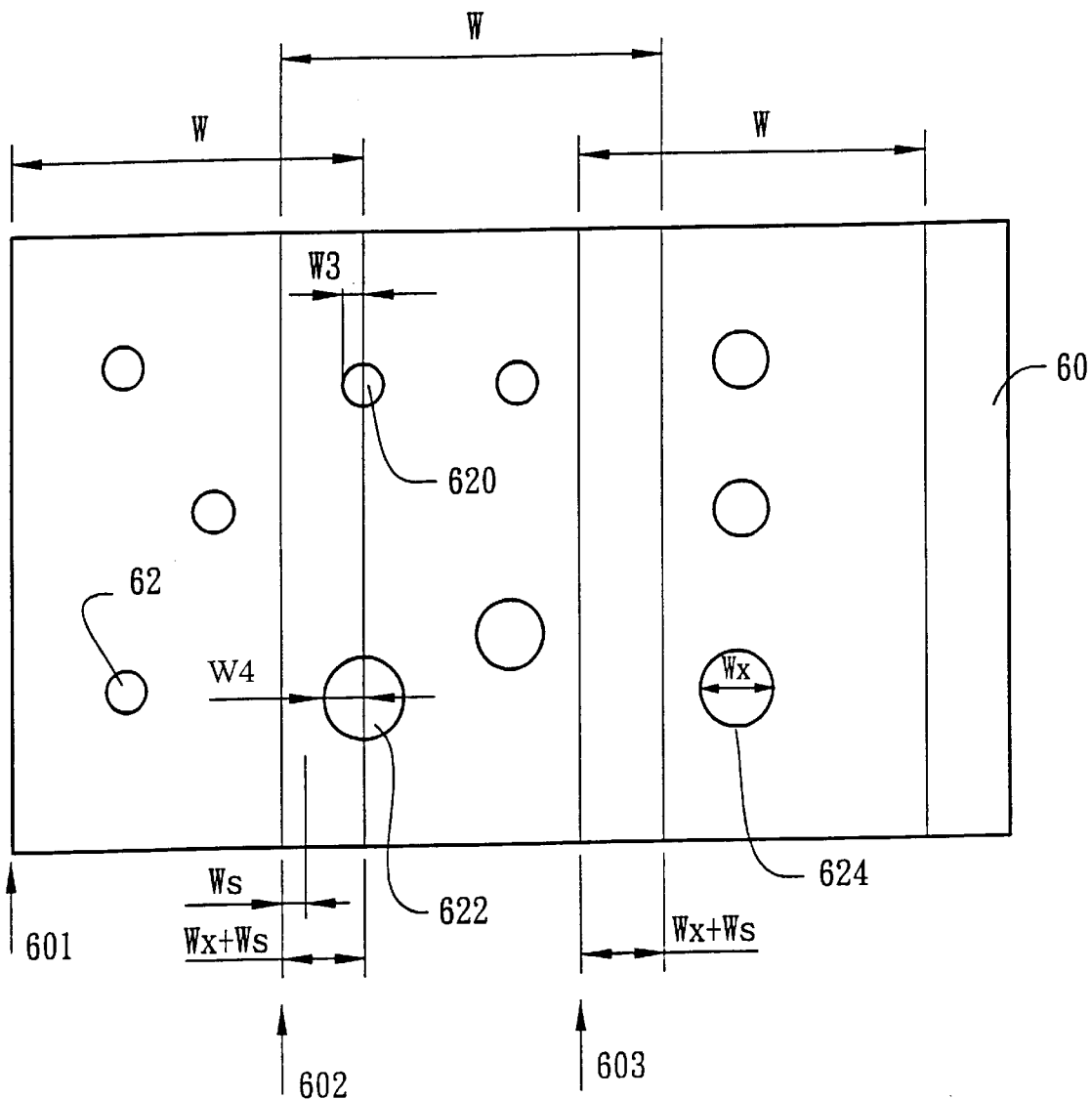
FIG. 5 is a diagram showing how to set intervals according to another simple embodiment of the present invention.

Please refer to FIGS. 3 to 5. As shown in FIG. 3, an initial scanning position (the initial position 501 of the first interval in FIG. 4 or the initial position 601 of the first interval in FIG. 5) is set in Step 40 shown in FIG. 3. The positive direction of the coordinates in FIGS. 4 and 5 is rightward. After the first interval is scanned, the initial scanning position of the next interval (the initial position 502 of the second interval in FIG. 4 or the initial position 602 of the second interval in FIG. 5) is set in Step 41 shown in FIG. 3. According to the above flowchart, the present invention proposes two detecting methods. FIG. 4 shows the first detecting method according to a preferred embodiment of the present invention. The width of each scan of the optical scanning tool 10 is set to a fixed width W acceptable to the signal receiver 16. When the first interval of a PCB 50 is scanned, drilled holes 520 and 522 are exactly situated on the boundary of the scanned interval. The distance between the drilled hole 520 and the boundary of the scanned interval is W1, while the distance between the drilled hole 522 and the boundary of the scanned interval is W2. Because W2 is larger than W1, W2 is selected as the setting basis. This way can be extended to situations when there are many drilled holes situated on the boundary of the scanned interval. The largest distance between the drilled holes and the boundary of the scanned interval will be selected as the setting basis. Ws is a predetermined safety distance to ensure that the drilled holes 520 and 522 can be completely scanned in the second interval so as to compensate the deviation of relative movement of the signal receiver 16 and the platform 20. Of course, Ws can also be set to zero. The initial position 502 of the second interval is the initial position 501 of the first interval plus the fixed width W, minus the setting basis W2, and then minus the safety distance Ws. Furthermore, when the second interval is scanned, because there is no drill hole such as 52 on the boundary of the scanned interval, it is only necessary to subtract the safety distance Ws. That is, the initial position 503 of the third interval is the initial position 502 of the second interval plus the fixed width W and then minus the safety distance Ws. The next step 42 is to judge whether the scanned interval is the last interval. If the answer is negative, Step 41 is jumped to set the initial scanning position of the next interval; otherwise, the process is stopped.

FIG. 5 shows the second detecting method according to a simple embodiment of the present invention. The width of each scan of the optical scanning tool 10 is again set to a fixed width W. When the first interval of a PCB 60 is scanned, drilled holes 620 and 622 are exactly situated on the boundary of the scanned interval. The distance between the drilled hole 620 and the boundary of the scanned interval is W3, while the distance between the drilled hole 622 and the boundary of the scanned interval is W4. As can be seen from the figure, W4 is larger than W3. However, because the diameter Wx of the drilled hole 624 is the largest on the PCB 60, Wx is selected as the setting basis. This information can be known in advance from the hole-drilling program or the CAD tool. Ws is a predetermined safety distance. The initial position 602 of the second interval is the initial position 601 of the first interval plus the fixed width W, minus the setting basis Wx, and then minus the safety distance Ws. Furthermore, when the second interval is scanned, although there is no drill hole such as 62 on the boundary of the scanned interval, it is necessary to add Ws to Wx as the width of the overlapped interval because the largest hole diameter Wx is the setting basis. That is, the initial position 603 of the third interval is the initial position 602 of the second interval plus the fixed width W, minus the largest hole diameter Wx, and then minus the safety distance Ws. Thereby, the initial position of each interval can be obtained. The distance between each interval is fixed to W-Wx-Ws in this method. Because the scanning process of this method is the same as that of the above method, they will not be further illustrated.

In the above first detecting method, the largest distance between drilled holes exactly situated on the boundary and the boundary of the scanned interval when scanning the previous interval is Wi (Wi can be zero, representing that there is no drilled hole on the boundary of the scanned interval). Wi plus a predetermined safety distance Ws (Ws can be zero) is the width of the overlapped interval of this scanned interval. The width of the overlapped interval of each scanned interval may be different. Although this way of calculation is more complex, because the width of the overlapped interval varies with Wi, the times of scanning will be the most adaptable. Therefore, the overall speed is faster. On the other hand, in the above second detecting method, the largest diameter of drilled holes on a PCB to be scanned is Wx (Wx can not be zero). Wx plus a predetermined safety distance Ws is the width of the overlapped interval of each scanned interval. That is, no matter whether there is any drilled hole on the boundary of the scanned interval, the same width of the overlapped interval is used for scanning. This way of calculation is simpler, but when there are more overlapped intervals, the times of scanning will increase, hence taking more time than the first detecting method.

After an interval is scanned, whether the interval is the last interval is judged. If the interval is not the last interval, the above procedures are repeated; otherwise, the scanning process is stopped.

Summing up, the present invention proposes an apparatus and two methods for detecting the accuracy of drilled holes on a PCB so that quick scanning of PCB's can be achieved.

Although the present invention has been described with reference to the preferred embodiments thereof, it will be understood that the invention is not limited to the details thereof. Various substitutions and modifications have suggested in the foregoing description, and other will occur to those of ordinary skill in the art. Therefore, all such substitutions and modifications are intended to be embraced within the scope of the invention as defined in the appended claims.

What is claimed is:

1. A method for detecting the accuracy of drilled holes in a PCB, comprising the steps of:

a. setting an initial scanning position, a safety distance and a fixed distance;

b. acquiring a largest distance value between a scanned interval boundary and holes situated on the scanned interval boundary;

c. adding the safety distance to the largest distance value obtained from step b to obtain a width of an overlapped interval;

d. adding the initial scanning position of a previous scanned interval and the fixed distance together, and then subtracting the width of the overlapped interval to obtain an initial scanning position of a next interval; and e. determining whether the present scanned interval is a last interval, if the present scanned interval is the last interval then the scanning process is stopped, and if the present scanned interval is not the last interval then steps b through e are repeated.

2. A method for detecting the accuracy of drilled holes in a PCB, comprising the steps of:

a. setting an initial scanning position, a safety distance and a fixed distance;

b. acquiring a largest diameter value of a hole in a PCB;

c. adding the safety distance to the largest diameter value obtained from step b to obtain a width of an overlapped interval;

d. adding an initial scanned position of a previous scanning interval and the fixed distance together, and then subtracting the width of the overlapped interval to obtain an initial scanning position of a next interval; and e. determining whether the present scanned interval is a last interval, if the present scanned interval is the last interval then the scanning process stopped, and if the present scanned interval is not the last interval then steps b through e are repeated.

\* \* \* \* \*